(12) United States Patent
Eisinger et al.

(10) Patent No.: US 11,241,233 B2
(45) Date of Patent: Feb. 8, 2022

(54) APPARATUS FOR ENSURING STRAIN GAUGE ACCURACY IN MEDICAL REUSABLE DEVICE

(71) Applicant: Covidien LP, Mansfield, MA (US)

(72) Inventors: Joseph Eisinger, Northford, CT (US); Patrick Mozdzierz, Glastonbury, CT (US); David Valentine, Hamden, CT (US); Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 258 days.

(21) Appl. No.: 16/441,625

(22) Filed: Jun. 14, 2019

(65) Prior Publication Data

US 2020/0015824 A1   Jan. 16, 2020

Related U.S. Application Data

(60) Provisional application No. 62/695,898, filed on Jul. 10, 2018.

(51) Int. Cl.
*A61B 17/068* (2006.01)
*A61B 17/115* (2006.01)
(Continued)

(52) U.S. Cl.
CPC ........ *A61B 17/1155* (2013.01); *A61B 17/068* (2013.01); *A61B 2017/00221* (2013.01);
(Continued)

(58) Field of Classification Search
CPC .............................................. A61B 2562/0261
See application file for complete search history.

(56) References Cited

U.S. PATENT DOCUMENTS

| 2,777,340 | 1/1957 | Hettwer et al. |
| 2,957,353 | 10/1960 | Babacz |

(Continued)

FOREIGN PATENT DOCUMENTS

| CA | 2451558 A1 | 1/2003 |
| CN | 1547454 A | 11/2004 |

(Continued)

OTHER PUBLICATIONS

Extended European Search Report corresponding to International Application No. EP 14 18 4882.0 dated May 12, 2015.
(Continued)

*Primary Examiner* — Eyamindae C Jallow

(57) ABSTRACT

An apparatus for ensuring strain gauge accuracy including a handle assembly including a controller, an adapter assembly including a tubular housing having a proximal end portion configured to couple to the handle assembly and a distal end portion, a load sensing assembly configured to measure a load exerted on the tubular housing, and a signal processing circuit electrically coupled to the load sensing assembly, a memory coupled to the signal processing circuit, and a calibration assembly including a biasing member having a known spring rate stored as a force value in the memory, the calibration assembly configured to couple to the distal end portion of the adapter assembly. The signal processing circuit is configured to calibrate the adapter assembly with the calibration assembly attached thereto by calculating a correction factor based on a comparison a force of the spring member measured by the load sensing assembly to the force value.

10 Claims, 10 Drawing Sheets

(51) Int. Cl.
    *A61B 17/00*      (2006.01)
    *A61B 17/072*     (2006.01)

(52) U.S. Cl.
    CPC .............. *A61B 2017/00393* (2013.01); *A61B 2017/00398* (2013.01); *A61B 2017/00473* (2013.01); *A61B 2017/00486* (2013.01); *A61B 2017/00734* (2013.01); *A61B 2017/07257* (2013.01); *A61B 2017/07271* (2013.01); *A61B 2017/07285* (2013.01)

(56) References Cited

U.S. PATENT DOCUMENTS

| | | |
|---|---|---|
| 3,111,328 | 11/1963 | Di Rito et al. |
| 3,695,058 | 10/1972 | Keith, Jr. |
| 3,734,515 | 5/1973 | Dudek |
| 3,759,336 | 9/1973 | Marcovitz et al. |
| 4,162,399 | 7/1979 | Hudson |
| 4,606,343 | 8/1986 | Conta et al. |
| 4,705,038 | 11/1987 | Sjostrom et al. |
| 4,722,685 | 2/1988 | de Estrada et al. |
| 4,823,807 | 4/1989 | Russell et al. |
| 4,874,181 | 10/1989 | Hsu |
| 5,129,118 | 7/1992 | Walmesley |
| 5,129,570 | 7/1992 | Schulze et al. |
| 5,152,744 | 10/1992 | Krause et al. |
| 5,301,061 | 4/1994 | Nakada et al. |
| 5,312,023 | 5/1994 | Green et al. |
| 5,326,013 | 7/1994 | Green et al. |
| 5,350,355 | 9/1994 | Sklar |
| 5,383,874 | 1/1995 | Jackson et al. |
| 5,383,880 | 1/1995 | Hooven |
| 5,389,098 | 2/1995 | Tsuruta et al. |
| 5,395,033 | 3/1995 | Byrne et al. |
| 5,400,267 | 3/1995 | Denen et al. |
| 5,411,508 | 5/1995 | Bessler et al. |
| 5,413,267 | 5/1995 | Solyntjes et al. |
| 5,427,087 | 6/1995 | Ito et al. |
| 5,433,721 | 7/1995 | Hooven et al. |
| 5,467,911 | 11/1995 | Tsuruta et al. |
| 5,476,379 | 12/1995 | Disel |
| 5,487,499 | 1/1996 | Sorrentino et al. |
| 5,518,163 | 5/1996 | Hooven |
| 5,518,164 | 5/1996 | Hooven |
| 5,526,822 | 6/1996 | Burbank et al. |
| 5,529,235 | 6/1996 | Boiarski et al. |
| 5,535,934 | 7/1996 | Boiarski et al. |
| 5,535,937 | 7/1996 | Boiarski et al. |
| 5,540,375 | 7/1996 | Bolanos et al. |
| 5,540,706 | 7/1996 | Aust et al. |
| 5,542,594 | 8/1996 | McKean et al. |
| 5,549,637 | 8/1996 | Crainich |
| 5,553,675 | 9/1996 | Pitzen et al. |
| 5,562,239 | 10/1996 | Boiarski et al. |
| 5,564,615 | 10/1996 | Bishop et al. |
| 5,609,560 | 3/1997 | Ichikawa et al. |
| 5,626,587 | 5/1997 | Bishop et al. |
| 5,632,432 | 5/1997 | Schulze et al. |
| 5,645,209 | 7/1997 | Green et al. |
| 5,647,526 | 7/1997 | Green et al. |
| 5,653,374 | 8/1997 | Young et al. |
| 5,658,300 | 8/1997 | Bito et al. |
| 5,662,662 | 9/1997 | Bishop et al. |
| 5,667,517 | 9/1997 | Hooven |
| 5,693,042 | 12/1997 | Boiarski et al. |
| 5,704,534 | 1/1998 | Huitema et al. |
| 5,713,505 | 2/1998 | Huitema |
| 5,762,603 | 6/1998 | Thompson |
| 5,779,130 | 7/1998 | Alesi et al. |
| 5,782,396 | 7/1998 | Mastri et al. |
| 5,782,397 | 7/1998 | Koukline |
| 5,792,573 | 8/1998 | Pitzen et al. |
| 5,797,536 | 8/1998 | Smith et al. |
| 5,820,009 | 10/1998 | Melling et al. |
| 5,863,159 | 1/1999 | Lasko |
| 5,865,361 | 2/1999 | Milliman et al. |
| 5,908,427 | 6/1999 | McKean et al. |
| 5,954,259 | 9/1999 | Viola et al. |
| 5,964,774 | 10/1999 | McKean et al. |
| 5,993,454 | 11/1999 | Longo |
| 6,010,054 | 1/2000 | Johnson et al. |
| 6,017,354 | 1/2000 | Culp et al. |
| 6,032,849 | 3/2000 | Mastri et al. |
| 6,045,560 | 4/2000 | McKean et al. |
| 6,090,123 | 7/2000 | Culp et al. |
| 6,126,651 | 10/2000 | Mayer |
| 6,129,547 | 10/2000 | Cise et al. |
| 6,165,169 | 12/2000 | Panescu et al. |
| 6,239,732 | 5/2001 | Cusey |
| 6,241,139 | 6/2001 | Milliman et al. |
| 6,264,086 | 7/2001 | McGuckin, Jr. |
| 6,264,087 | 7/2001 | Whitman |
| 6,302,311 | 10/2001 | Adams et al. |
| 6,315,184 | 11/2001 | Whitman |
| 6,321,855 | 11/2001 | Barnes |
| 6,329,778 | 12/2001 | Culp et al. |
| 6,343,731 | 2/2002 | Adams et al. |
| 6,348,061 | 2/2002 | Whitman |
| 6,368,324 | 4/2002 | Dinger et al. |
| 6,371,909 | 4/2002 | Hoeg et al. |
| 6,434,507 | 8/2002 | Clayton et al. |
| 6,443,973 | 9/2002 | Whitman |
| 6,461,372 | 10/2002 | Jensen et al. |
| 6,488,197 | 12/2002 | Whitman |
| 6,491,201 | 12/2002 | Whitman |
| 6,533,157 | 3/2003 | Whitman |
| 6,537,280 | 3/2003 | Dinger et al. |
| 6,610,066 | 8/2003 | Dinger et al. |
| 6,611,793 | 8/2003 | Burnside et al. |
| 6,645,218 | 11/2003 | Cassidy et al. |
| 6,654,999 | 12/2003 | Stoddard et al. |
| 6,698,643 | 3/2004 | Whitman |
| 6,699,177 | 3/2004 | Wang et al. |
| 6,716,233 | 4/2004 | Whitman |
| 6,743,240 | 6/2004 | Smith et al. |
| 6,783,533 | 8/2004 | Green et al. |
| 6,792,390 | 9/2004 | Burnside et al. |
| 6,793,652 | 9/2004 | Whitman et al. |
| 6,817,508 | 11/2004 | Racenet et al. |
| 6,830,174 | 12/2004 | Hillstead et al. |
| 6,846,308 | 1/2005 | Whitman et al. |
| 6,846,309 | 1/2005 | Whitman et al. |
| 6,849,071 | 2/2005 | Whitman et al. |
| 6,860,892 | 3/2005 | Tanaka et al. |
| 6,899,538 | 5/2005 | Matoba |
| 6,905,057 | 6/2005 | Swayze et al. |
| 6,959,852 | 11/2005 | Shelton, IV et al. |
| 6,964,363 | 11/2005 | Wales et al. |
| 6,981,628 | 1/2006 | Wales |
| 6,981,941 | 1/2006 | Whitman et al. |
| 6,986,451 | 1/2006 | Mastri et al. |
| 6,988,649 | 1/2006 | Shelton, IV et al. |
| 7,032,798 | 4/2006 | Whitman et al. |
| RE39,152 | 6/2006 | Aust et al. |
| 7,055,731 | 6/2006 | Shelton, IV et al. |
| 7,059,508 | 6/2006 | Shelton, IV et al. |
| 7,077,856 | 7/2006 | Whitman |
| 7,111,769 | 9/2006 | Wales et al. |
| 7,122,029 | 10/2006 | Koop et al. |
| 7,140,528 | 11/2006 | Shelton, IV |
| 7,141,049 | 11/2006 | Stern et al. |
| 7,143,923 | 12/2006 | Shelton, IV et al. |
| 7,143,925 | 12/2006 | Shelton, IV et al. |
| 7,143,926 | 12/2006 | Shelton, IV et al. |
| 7,147,138 | 12/2006 | Shelton, IV |
| 7,172,104 | 2/2007 | Scirica et al. |
| 7,225,964 | 6/2007 | Mastri et al. |
| 7,238,021 | 7/2007 | Johnson |
| 7,246,734 | 7/2007 | Shelton, IV |
| 7,252,660 | 8/2007 | Kunz |
| 7,328,828 | 2/2008 | Ortiz et al. |
| 7,364,061 | 4/2008 | Swayze et al. |
| 7,380,695 | 6/2008 | Doll et al. |
| 7,380,696 | 6/2008 | Shelton, IV et al. |

(56) References Cited

U.S. PATENT DOCUMENTS

| | | |
|---|---|---|
| 7,404,508 | 7/2008 | Smith et al. |
| 7,407,078 | 8/2008 | Shelton, IV et al. |
| 7,416,101 | 8/2008 | Shelton, IV et al. |
| 7,419,080 | 9/2008 | Smith et al. |
| 7,422,139 | 9/2008 | Shelton, IV et al. |
| 7,431,189 | 10/2008 | Shelton, IV et al. |
| 7,441,684 | 10/2008 | Shelton, IV et al. |
| 7,448,525 | 11/2008 | Shelton, IV et al. |
| 7,464,846 | 12/2008 | Shelton, IV et al. |
| 7,464,847 | 12/2008 | Viola et al. |
| 7,464,849 | 12/2008 | Shelton, IV et al. |
| 7,481,347 | 1/2009 | Roy |
| 7,481,824 | 1/2009 | Boudreaux et al. |
| 7,487,899 | 2/2009 | Shelton, IV et al. |
| 7,549,564 | 6/2009 | Boudreaux |
| 7,565,993 | 7/2009 | Milliman et al. |
| 7,568,603 | 8/2009 | Shelton, IV et al. |
| 7,575,144 | 8/2009 | Ortiz et al. |
| 7,588,175 | 9/2009 | Timm et al. |
| 7,588,176 | 9/2009 | Timm et al. |
| 7,637,409 | 12/2009 | Marczyk |
| 7,641,093 | 1/2010 | Doll et al. |
| 7,644,848 | 1/2010 | Swayze et al. |
| 7,670,334 | 3/2010 | Hueil et al. |
| 7,673,780 | 3/2010 | Shelton, IV et al. |
| 7,699,835 | 4/2010 | Lee et al. |
| 7,721,931 | 5/2010 | Shelton, IV et al. |
| 7,738,971 | 6/2010 | Swayze et al. |
| 7,740,159 | 6/2010 | Shelton, IV et al. |
| 7,743,960 | 6/2010 | Whitman et al. |
| 7,758,613 | 7/2010 | Whitman |
| 7,766,210 | 8/2010 | Shelton, IV et al. |
| 7,770,773 | 8/2010 | Whitman et al. |
| 7,770,775 | 8/2010 | Shelton, IV et al. |
| 7,793,812 | 9/2010 | Moore et al. |
| 7,799,039 | 9/2010 | Shelton, IV et al. |
| 7,802,712 | 9/2010 | Milliman et al. |
| 7,803,151 * | 9/2010 | Whitman .......... A61B 90/98 606/1 |
| 7,822,458 | 10/2010 | Webster, III et al. |
| 7,845,534 | 12/2010 | Viola et al. |
| 7,845,537 | 12/2010 | Shelton, IV et al. |
| 7,857,185 | 12/2010 | Swayze et al. |
| 7,870,989 | 1/2011 | Viola et al. |
| 7,900,805 | 3/2011 | Shelton, IV et al. |
| 7,905,897 | 3/2011 | Whitman et al. |
| 7,918,230 | 4/2011 | Whitman et al. |
| 7,922,061 | 4/2011 | Shelton, IV et al. |
| 7,922,719 | 4/2011 | Ralph et al. |
| 7,947,034 | 5/2011 | Whitman |
| 7,951,071 | 5/2011 | Whitman et al. |
| 7,954,682 | 6/2011 | Giordano et al. |
| 7,959,051 | 6/2011 | Smith et al. |
| 7,963,433 | 6/2011 | Whitman et al. |
| 7,967,178 | 6/2011 | Scirica et al. |
| 7,967,179 | 6/2011 | Olson et al. |
| 7,992,758 | 8/2011 | Whitman et al. |
| 8,011,550 | 9/2011 | Aranyi et al. |
| 8,016,178 | 9/2011 | Olson et al. |
| 8,016,855 | 9/2011 | Whitman et al. |
| 8,020,743 | 9/2011 | Shelton, IV |
| 8,025,199 | 9/2011 | Whitman et al. |
| 8,035,487 | 10/2011 | Malackowski |
| 8,052,024 | 11/2011 | Viola et al. |
| 8,056,787 | 11/2011 | Boudreaux et al. |
| 8,114,118 | 2/2012 | Knodel et al. |
| 8,127,975 | 3/2012 | Olson et al. |
| 8,132,705 | 3/2012 | Viola et al. |
| 8,152,516 | 4/2012 | Harvey et al. |
| 8,157,150 | 4/2012 | Viola et al. |
| 8,157,151 | 4/2012 | Ingmanson et al. |
| 8,182,494 | 5/2012 | Yencho et al. |
| 8,186,555 | 5/2012 | Shelton, IV et al. |
| 8,186,587 | 5/2012 | Zmood et al. |
| 8,220,367 | 7/2012 | Hsu |
| 8,235,273 | 8/2012 | Olson et al. |
| 8,241,322 | 8/2012 | Whitman et al. |
| 8,272,554 | 9/2012 | Whitman et al. |
| 8,292,150 | 10/2012 | Bryant |
| 8,292,888 | 10/2012 | Whitman |
| 8,303,581 | 11/2012 | Arts et al. |
| 8,342,379 | 1/2013 | Whitman et al. |
| 8,348,130 | 1/2013 | Shah et al. |
| 8,348,855 | 1/2013 | Hillely et al. |
| 8,353,440 | 1/2013 | Whitman et al. |
| 8,357,144 | 1/2013 | Whitman et al. |
| 8,365,633 | 2/2013 | Simaan et al. |
| 8,365,972 | 2/2013 | Aranyi et al. |
| 8,371,492 | 2/2013 | Aranyi et al. |
| 8,372,057 | 2/2013 | Cude et al. |
| 8,391,957 | 3/2013 | Carlson et al. |
| 8,403,926 | 3/2013 | Nobis et al. |
| 8,403,949 | 3/2013 | Palmer et al. |
| 8,418,904 | 4/2013 | Wenchell et al. |
| 8,424,739 | 4/2013 | Racenet et al. |
| 8,454,585 | 6/2013 | Whitman |
| 8,505,802 | 8/2013 | Viola et al. |
| 8,517,241 | 8/2013 | Nicholas et al. |
| 8,523,043 | 9/2013 | Ullrich et al. |
| 8,551,076 | 10/2013 | Duval et al. |
| 8,561,871 | 10/2013 | Rajappa et al. |
| 8,561,874 | 10/2013 | Scirica |
| 8,602,287 | 12/2013 | Yates et al. |
| 8,623,000 | 1/2014 | Humayun et al. |
| 8,627,995 | 1/2014 | Smith et al. |
| 8,632,463 | 1/2014 | Drinan et al. |
| 8,636,766 | 1/2014 | Milliman et al. |
| 8,647,258 | 2/2014 | Aranyi et al. |
| 8,652,121 | 2/2014 | Quick et al. |
| 8,657,174 | 2/2014 | Yates et al. |
| 8,657,177 | 2/2014 | Scirica et al. |
| 8,672,206 | 3/2014 | Aranyi et al. |
| 8,696,552 | 4/2014 | Whitman |
| 8,708,213 | 4/2014 | Shelton, IV et al. |
| 8,715,306 | 5/2014 | Faller et al. |
| 8,752,749 | 6/2014 | Moore et al. |
| 8,758,391 | 6/2014 | Swayze et al. |
| 8,806,973 | 8/2014 | Ross et al. |
| 8,808,311 | 8/2014 | Heinrich et al. |
| 8,820,605 | 9/2014 | Shelton, IV |
| 8,851,355 | 10/2014 | Aranyi et al. |
| 8,858,571 | 10/2014 | Shelton, IV et al. |
| 8,875,972 | 11/2014 | Weisenburgh, II et al. |
| 8,888,762 | 11/2014 | Whitman |
| 8,893,946 | 11/2014 | Boudreaux et al. |
| 8,899,462 | 12/2014 | Kostrzewski et al. |
| 8,905,289 | 12/2014 | Patel et al. |
| 8,919,630 | 12/2014 | Milliman |
| 8,931,680 | 1/2015 | Milliman |
| 8,939,344 | 1/2015 | Olson et al. |
| 8,950,646 | 2/2015 | Viola |
| 8,960,519 | 2/2015 | Whitman et al. |
| 8,961,396 | 2/2015 | Azarbarzin et al. |
| 8,967,443 | 3/2015 | McCuen |
| 8,968,276 | 3/2015 | Zemlok et al. |
| 8,968,337 | 3/2015 | Whitfield et al. |
| 8,992,422 | 3/2015 | Spivey et al. |
| 9,016,545 | 4/2015 | Aranyi et al. |
| 9,023,014 | 5/2015 | Chowaniec et al. |
| 9,033,868 | 5/2015 | Whitman et al. |
| 9,055,943 | 6/2015 | Zemlok et al. |
| 9,064,653 | 6/2015 | Prest et al. |
| 9,072,515 | 7/2015 | Hall et al. |
| 9,113,847 | 8/2015 | Whitman et al. |
| 9,113,875 | 8/2015 | Viola et al. |
| 9,113,876 | 8/2015 | Zemlok et al. |
| 9,113,899 | 8/2015 | Garrison et al. |
| 9,216,013 | 12/2015 | Scirica et al. |
| 9,241,712 | 1/2016 | Zemlok et al. |
| 9,282,961 | 3/2016 | Whitman et al. |
| 9,282,963 | 3/2016 | Bryant |
| 9,295,522 | 3/2016 | Kostrzewski |
| 9,307,986 | 4/2016 | Hall et al. |
| 2001/0031975 | 10/2001 | Whitman et al. |

(56) References Cited

U.S. PATENT DOCUMENTS

| | | |
|---|---|---|
| 2002/0049454 | 4/2002 | Whitman et al. |
| 2002/0165541 | 11/2002 | Whitman |
| 2003/0038938 | 2/2003 | Jung et al. |
| 2003/0165794 | 9/2003 | Matoba |
| 2004/0034369 | 2/2004 | Sauer et al. |
| 2004/0111012 | 6/2004 | Whitman |
| 2004/0133189 | 7/2004 | Sakurai |
| 2004/0153124 | 8/2004 | Whitman |
| 2004/0176751 | 9/2004 | Weitzner et al. |
| 2004/0193146 | 9/2004 | Lee et al. |
| 2005/0125027 | 6/2005 | Knodel et al. |
| 2005/0131442 | 6/2005 | Yachia et al. |
| 2006/0142656 | 6/2006 | Malackowski et al. |
| 2006/0142740 | 6/2006 | Sherman et al. |
| 2006/0142744 | 6/2006 | Boutoussov |
| 2006/0259073 | 11/2006 | Miyamoto et al. |
| 2006/0278680 | 12/2006 | Viola et al. |
| 2006/0284730 | 12/2006 | Schmid et al. |
| 2007/0023476 | 2/2007 | Whitman et al. |
| 2007/0023477 | 2/2007 | Whitman et al. |
| 2007/0027469 | 2/2007 | Smith et al. |
| 2007/0029363 | 2/2007 | Popov |
| 2007/0084897 | 4/2007 | Shelton et al. |
| 2007/0102472 | 5/2007 | Shelton |
| 2007/0152014 | 7/2007 | Gillum et al. |
| 2007/0175947 | 8/2007 | Ortiz et al. |
| 2007/0175949 | 8/2007 | Shelton et al. |
| 2007/0175950 | 8/2007 | Shelton et al. |
| 2007/0175951 | 8/2007 | Shelton et al. |
| 2007/0175955 | 8/2007 | Shelton et al. |
| 2007/0270784 | 11/2007 | Smith et al. |
| 2008/0029570 | 2/2008 | Shelton et al. |
| 2008/0029573 | 2/2008 | Shelton et al. |
| 2008/0029574 | 2/2008 | Shelton et al. |
| 2008/0029575 | 2/2008 | Shelton et al. |
| 2008/0058801 | 3/2008 | Taylor et al. |
| 2008/0109012 | 5/2008 | Falco et al. |
| 2008/0110958 | 5/2008 | McKenna et al. |
| 2008/0147089 | 6/2008 | Loh et al. |
| 2008/0167736 | 7/2008 | Swayze et al. |
| 2008/0185419 | 8/2008 | Smith et al. |
| 2008/0188841 | 8/2008 | Tomasello et al. |
| 2008/0197167 | 8/2008 | Viola et al. |
| 2008/0208195 | 8/2008 | Shores et al. |
| 2008/0237296 | 10/2008 | Boudreaux et al. |
| 2008/0245841 * | 10/2008 | Smith ............... A61B 17/1114 227/175.2 |
| 2008/0251561 | 10/2008 | Eades et al. |
| 2008/0255413 | 10/2008 | Zemlok et al. |
| 2008/0255607 | 10/2008 | Zemlok |
| 2008/0262654 | 10/2008 | Omori et al. |
| 2008/0308603 | 12/2008 | Shelton et al. |
| 2009/0012533 | 1/2009 | Barbagli et al. |
| 2009/0090763 | 4/2009 | Zemlok et al. |
| 2009/0099876 * | 4/2009 | Whitman ............... G06Q 10/10 705/3 |
| 2009/0138006 | 5/2009 | Bales et al. |
| 2009/0171147 | 7/2009 | Lee et al. |
| 2009/0182193 | 7/2009 | Whitman et al. |
| 2009/0209946 | 8/2009 | Swayze et al. |
| 2009/0209990 | 8/2009 | Yates et al. |
| 2009/0254094 | 10/2009 | Knapp et al. |
| 2009/0299141 | 12/2009 | Downey et al. |
| 2010/0023022 | 1/2010 | Zeiner et al. |
| 2010/0069942 | 3/2010 | Shelton, IV |
| 2010/0193568 | 8/2010 | Scheib et al. |
| 2010/0211053 | 8/2010 | Ross et al. |
| 2010/0225073 | 9/2010 | Porter et al. |
| 2011/0006101 | 1/2011 | Hall et al. |
| 2011/0017801 | 1/2011 | Zemlok et al. |
| 2011/0071508 | 3/2011 | Duval et al. |
| 2011/0077673 | 3/2011 | Grubac et al. |
| 2011/0121049 | 5/2011 | Malinouskas et al. |
| 2011/0125138 | 5/2011 | Malinouskas et al. |
| 2011/0139851 | 6/2011 | McCuen |
| 2011/0153252 | 6/2011 | Govari et al. |
| 2011/0155783 | 6/2011 | Rajappa et al. |
| 2011/0155786 | 6/2011 | Shelton, IV |
| 2011/0172648 | 7/2011 | Jeong |
| 2011/0174009 | 7/2011 | Iizuka et al. |
| 2011/0174099 | 7/2011 | Ross et al. |
| 2011/0184245 | 7/2011 | Xia et al. |
| 2011/0204119 | 8/2011 | McCuen |
| 2011/0218522 | 9/2011 | Whitman |
| 2011/0276057 | 11/2011 | Conlon et al. |
| 2011/0290854 | 12/2011 | Timm et al. |
| 2011/0295242 | 12/2011 | Spivey et al. |
| 2011/0295269 | 12/2011 | Swensgard et al. |
| 2012/0000962 | 1/2012 | Racenet et al. |
| 2012/0074199 | 3/2012 | Olson et al. |
| 2012/0089131 | 4/2012 | Zemlok et al. |
| 2012/0104071 | 5/2012 | Bryant |
| 2012/0116368 | 5/2012 | Viola |
| 2012/0143002 | 6/2012 | Aranyi et al. |
| 2012/0172924 | 7/2012 | Allen, IV |
| 2012/0211542 | 8/2012 | Racenet |
| 2012/0223121 | 9/2012 | Viola et al. |
| 2012/0245428 | 9/2012 | Smith et al. |
| 2012/0253329 | 10/2012 | Zemlok et al. |
| 2012/0310220 | 12/2012 | Malkowski et al. |
| 2012/0323226 | 12/2012 | Chowaniec et al. |
| 2012/0330285 | 12/2012 | Hartoumbekis et al. |
| 2013/0093149 | 4/2013 | Saur et al. |
| 2013/0181035 | 7/2013 | Milliman |
| 2013/0184704 | 7/2013 | Beardsley et al. |
| 2013/0214025 | 8/2013 | Zemlok et al. |
| 2013/0274722 | 10/2013 | Kostrzewski et al. |
| 2013/0282052 | 10/2013 | Aranyi et al. |
| 2013/0292451 | 11/2013 | Viola et al. |
| 2013/0313304 | 11/2013 | Shelton, IV et al. |
| 2013/0317486 | 11/2013 | Nicholas et al. |
| 2013/0319706 | 12/2013 | Nicholas et al. |
| 2013/0324978 | 12/2013 | Nicholas et al. |
| 2013/0324979 | 12/2013 | Nicholas et al. |
| 2013/0334281 | 12/2013 | Williams |
| 2014/0012236 | 1/2014 | Williams et al. |
| 2014/0012237 | 1/2014 | Pribanic et al. |
| 2014/0012289 | 1/2014 | Snow et al. |
| 2014/0025046 | 1/2014 | Williams et al. |
| 2014/0110455 | 4/2014 | Ingmanson et al. |
| 2014/0207125 | 7/2014 | Applegate et al. |
| 2014/0207182 | 7/2014 | Zergiebel et al. |
| 2014/0207185 | 7/2014 | Goble et al. |
| 2014/0236174 | 8/2014 | Williams et al. |
| 2014/0276932 | 9/2014 | Williams et al. |
| 2014/0299647 | 10/2014 | Scirica et al. |
| 2014/0303668 | 10/2014 | Nicholas et al. |
| 2014/0358129 | 12/2014 | Zergiebel et al. |
| 2014/0361068 | 12/2014 | Aranyi et al. |
| 2014/0365235 | 12/2014 | DeBoer et al. |
| 2014/0373652 | 12/2014 | Zergiebel et al. |
| 2015/0014392 | 1/2015 | Williams et al. |
| 2015/0048144 | 2/2015 | Whitman |
| 2015/0076205 | 3/2015 | Zergiebel |
| 2015/0080912 | 3/2015 | Sapre |
| 2015/0112381 | 4/2015 | Richard |
| 2015/0122870 | 5/2015 | Zemlok et al. |
| 2015/0133224 | 5/2015 | Whitman et al. |
| 2015/0150547 | 6/2015 | Ingmanson et al. |
| 2015/0150574 | 6/2015 | Richard et al. |
| 2015/0157320 | 6/2015 | Zergiebel et al. |
| 2015/0157321 * | 6/2015 | Zergiebel ......... A61B 17/07207 227/175.1 |
| 2015/0164502 | 6/2015 | Richard et al. |
| 2015/0201931 | 7/2015 | Zergiebel et al. |
| 2015/0272577 | 10/2015 | Zemlok et al. |
| 2015/0297199 | 10/2015 | Nicholas et al. |
| 2015/0303996 | 10/2015 | Calderoni |
| 2015/0316431 * | 11/2015 | Collins .................. G01L 5/0028 606/219 |
| 2015/0320420 | 11/2015 | Penna et al. |
| 2015/0327850 | 11/2015 | Kostrzewski |
| 2015/0342601 | 12/2015 | Williams et al. |
| 2015/0342603 | 12/2015 | Zergiebel et al. |

(56) References Cited

U.S. PATENT DOCUMENTS

| | | | |
|---|---|---|---|
| 2015/0351765 | * | 12/2015 | Valentine ............ G06F 11/1448 227/176.1 |
| 2015/0374366 | | 12/2015 | Zergiebel et al. |
| 2015/0374370 | | 12/2015 | Zergiebel et al. |
| 2015/0374371 | | 12/2015 | Richard et al. |
| 2015/0374372 | | 12/2015 | Zergiebel et al. |
| 2015/0374449 | | 12/2015 | Chowaniec et al. |
| 2015/0380187 | | 12/2015 | Zergiebel et al. |
| 2016/0015937 | * | 1/2016 | Hart ...................... A61B 34/71 604/95.04 |
| 2016/0066909 | | 3/2016 | Baber et al. |
| 2016/0066916 | * | 3/2016 | Overmyer .............. A61B 17/32 227/176.1 |
| 2016/0095585 | | 4/2016 | Zergiebel et al. |
| 2016/0095596 | | 4/2016 | Scirica et al. |
| 2016/0106406 | | 4/2016 | Cabrera et al. |
| 2016/0113648 | | 4/2016 | Zergiebel et al. |
| 2016/0113649 | | 4/2016 | Zergiebel et al. |
| 2016/0310134 | | 10/2016 | Contini et al. |
| 2016/0374668 | * | 12/2016 | Measamer ......... A61B 17/1155 227/175.1 |
| 2017/0164947 | | 6/2017 | Williams |
| 2017/0296178 | * | 10/2017 | Miller ..................... A61B 5/05 |
| 2018/0043098 | * | 2/2018 | Ottolino ............... A61B 5/4824 |
| 2018/0353186 | * | 12/2018 | Mozdzierz ......... A61B 17/1155 |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated April 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.
Extended European Search Report dated Feb. 3, 2020 corresponding to counterpart Patent Application EP 19185184.9.

* cited by examiner

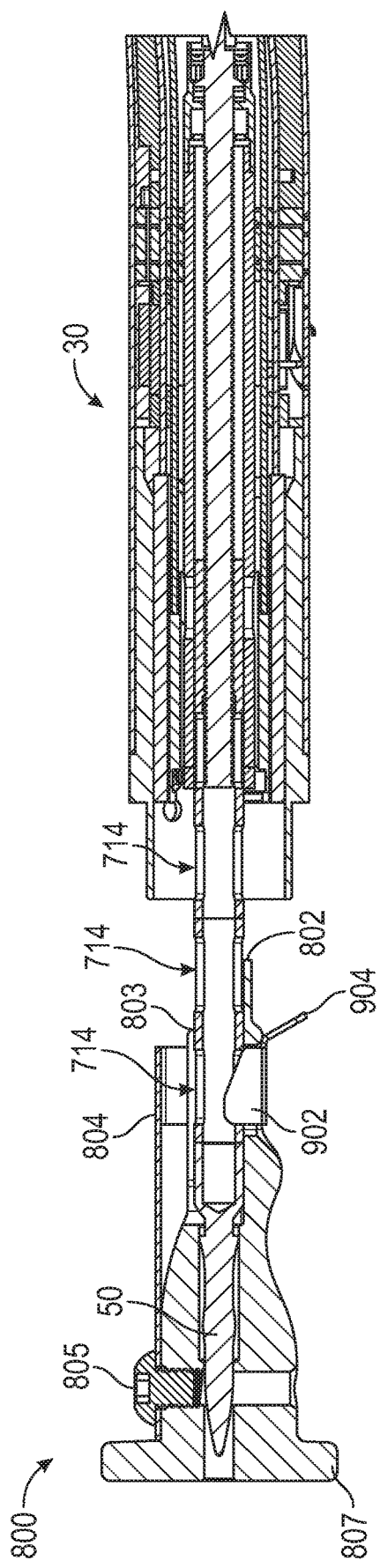
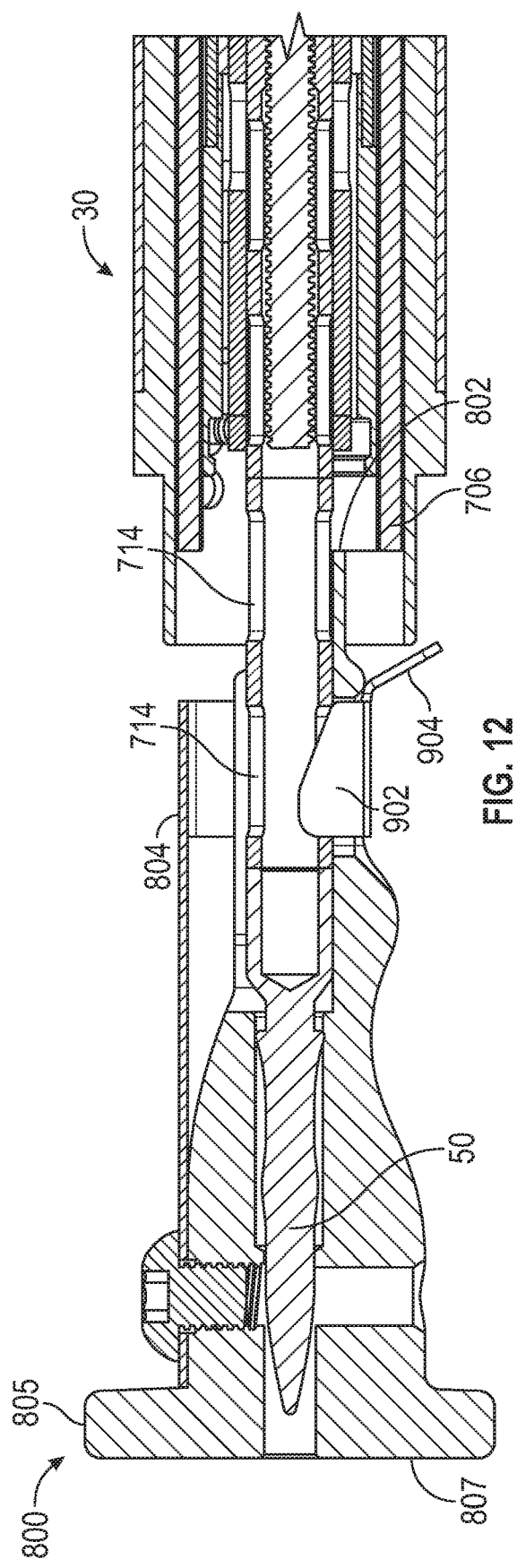

APPARATUS FOR ENSURING STRAIN GAUGE ACCURACY IN MEDICAL REUSABLE DEVICE

CROSS-REFERENCE TO RELATED APPLICATIONS

This application claims the benefit of and priority to U.S. Provisional Patent Application No. 62/695,898 filed Jul. 10, 2018, the entire disclosure of which is incorporated by reference herein.

BACKGROUND

1. Technical Field

The present disclosure relates to surgical instrument. More specifically, the present disclosure relates to ensuring accuracy of load sensing devices used in handheld electromechanical surgical systems.

2. Background of Related Art

One type of surgical instrument is a circular clamping, cutting and stapling device. Such a device may be employed in a surgical procedure to reattach rectum portions that were previously transected, or similar procedures. Conventional circular clamping, cutting, and stapling devices include a pistol or linear grip-styled structure having an elongated shaft extending therefrom and a staple cartridge supported on the distal end of the elongated shaft. In this instance, a physician may insert an anvil assembly of the circular stapling device into a rectum of a patient and maneuver the anvil assembly up the colonic tract of the patient toward the transected rectum portions. The physician may also insert the remainder of the circular stapling device (including the cartridge assembly) through an incision and toward the transected rectum portions. The anvil and cartridge assemblies are approximated toward one another and staples are ejected from the cartridge assembly toward the anvil assembly thereby forming the staples in tissue to affect an end-to-end anastomosis, and an annular knife is fired to core a portion of the clamped tissue portions. After the end-to-end anastomosis has been effected, the circular stapling device is removed from the surgical site.

A number of surgical instrument manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical instruments and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical instruments and/or handle assemblies that use rotary motion.

In order to make the linear driven end effectors compatible with powered surgical instruments that use a rotary motion to deliver power, a need exists for adapters to interconnect the linear driven end effectors with the powered rotary driven surgical instruments. Due to powered actuation of these adapters and end effectors various sensors are used to measure mechanical forces and strain imparted on them during use. Accordingly, there is a need for systems and methods to calibrate and/or verify operation of these sensors.

SUMMARY

Powered surgical instruments may include various sensors for providing feedback during their operation. Feedback detection enables anvil detection, staple detection, cutting to a force for consistent cutting, controlled tissue compression to avoid tissue damage while maximizing staple formation consistency, excessive load adjustment of stroke to optimized staple formation, and tissue thickness identification. Use of load sensing devices, such as strain gauges, in reusable devices enables many powered, reusable, intelligent devices. Maintaining load sensing device calibration ensures accurate readings or measurements. This device calibration enables a higher degree of load sensing device accuracy confidence, than that gained through reliability testing. This greater confidence may enable load sensing devices, that are unable to establish statistical reliability, to be reused in the field without risk to the patient.

The present disclosure provides for a calibration assembly having accurate feedback detection. This eliminates the problem of un-calibrated feedback detection and the need for reliability testing, which is required to prove that the load sensing device reading correlation to actual forces maintains accuracy. The apparatus incorporates an external fixture to enable the adapter to check the load sensing device accuracy.

According to one embodiment of the present disclosure, an apparatus for ensuring strain gauge accuracy is disclosed. The apparatus includes a handle assembly including a controller, an adapter assembly including a tubular housing having a proximal end portion configured to couple to the handle assembly and a distal end portion, a load sensing assembly configured to measure a load exerted on the tubular housing, and a signal processing circuit electrically coupled to the load sensing assembly, a memory coupled to the signal processing circuit, and a calibration assembly including a biasing member having a known spring rate stored as a force value in the memory, the calibration assembly configured to couple to the distal end portion of the adapter assembly. The signal processing circuit is configured to calibrate the adapter assembly with the calibration assembly attached thereto by calculating a correction factor based on a comparison a force of the spring member measured by the load sensing assembly to the force value.

According to one aspect of the above embodiments, the memory stores the force measured by the load sensing assembly and the correction factor. According to another aspect of the present disclosure the handle assembly includes a display and the controller is configured to display the correction factor on the display. According to a further embodiment of the present disclosure, the biasing member is selectable from a plurality of biasing members and is selectively couplable to the calibration assembly. According to another aspect of the present disclosure the correction factor is used to adjust a measurement by the load sensing assembly during use of the apparatus.

According to one embodiment of the present disclosure, an apparatus for ensuring strain gauge accuracy is disclosed. The apparatus includes a handle assembly including a controller, an adapter assembly which includes a tubular housing having a proximal end portion configured to couple to the handle assembly and a distal end portion, a load sensing assembly configured to measure a load exerted on the tubular housing, and a signal processing circuit electrically coupled to the load sensing assembly, a memory coupled to the signal processing circuit, the memory storing at least one strain value, and a calibration assembly including a hard stop that the adapter assembly, the calibration assembly configured to couple to the distal end portion of the adapter assembly, such that the adapter assembly flexes under load while applying pressure on the hard stop. The signal processing circuit is configured to calibrate the adapter assembly with the calibration assembly attached thereto by calculating a correction factor based on a deviation between the at least one strain value and a force value measured by the load sensing assembly during flexing of the adapter assembly under load while applying pressure on the hard stop.

According to one aspect of the above embodiments, the memory stores the correction factor. According to another aspect of the above embodiments, the correction factor is used to correct at least one strain value. According to a further aspect of the above embodiments, the handle assembly includes a display and the controller is configured to display the correction factor on the display. The correction factor is used to adjust a measurement by the load sensing assembly during use of the apparatus.

BRIEF DESCRIPTION OF THE DRAWINGS

Embodiments of the present disclosure are described herein with reference to the accompanying drawings, wherein:

FIG. 11 is a side, cross-sectional view, of the distal end portion of the adapter assembly of FIG. 1 coupled with the calibration assembly of FIG. 10, where the trocar member is extended, according to an embodiment the present disclosure;

FIG. 12 is a side, cross-sectional view, of the distal end portion of the adapter assembly of FIG. 1 coupled with the calibration assembly of FIG. 10, where the staple band is extended to contact the calibration assembly, according to an embodiment the present disclosure;

DETAILED DESCRIPTION OF EMBODIMENTS

Figure 1:
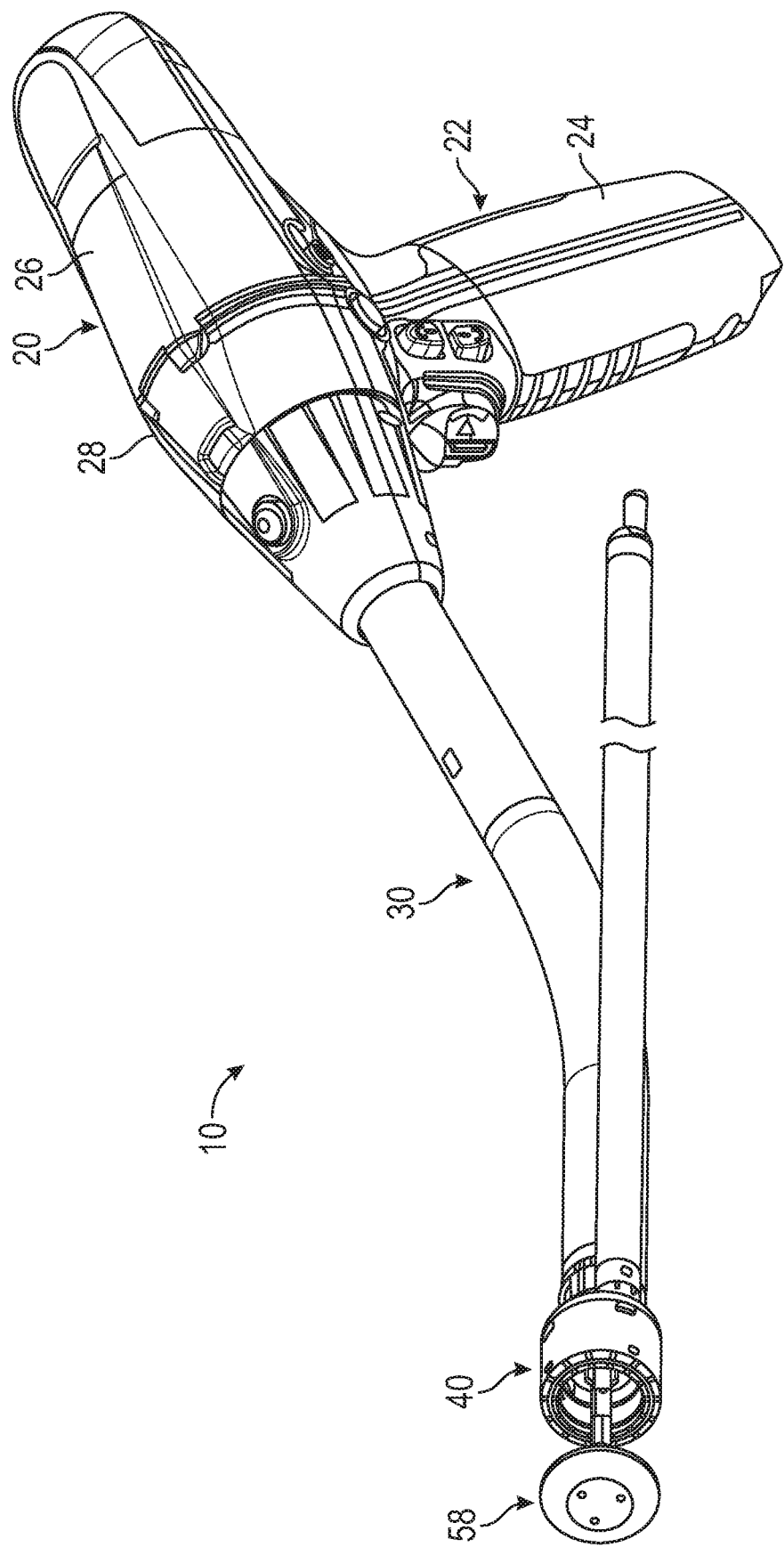
FIG. 1 is a perspective view of a handheld surgical instrument, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to powered surgical instruments having electronic sensors for monitoring mechanical strain and forces imparted on components of the powered surgical instruments. More particularly, this disclosure relates to load measuring sensors including load sensing devices as well as analog and digital circuitry that are hermetically sealed such that the load sensors are configured to resist harsh environments. In the event that electrical connections of the powered surgical instruments are compromised during use, measurement signals output by the sensors of the present disclosure remain unaltered. In addition, the sensors are programmable allowing for adjustments to gain and offset values in order to optimize the measurement signals.

With reference to FIG. 1, a powered surgical instrument 10 includes a handle assembly 20, which is configured for selective connection with an adapter assembly 30, which in turn, is configured for selective connection with an end effector, such as an annular reload 40. Although generally referred to as being a powered surgical instrument, it is contemplated that the surgical instrument 10 may be a manually actuated and may include various configurations.

Figure 2:
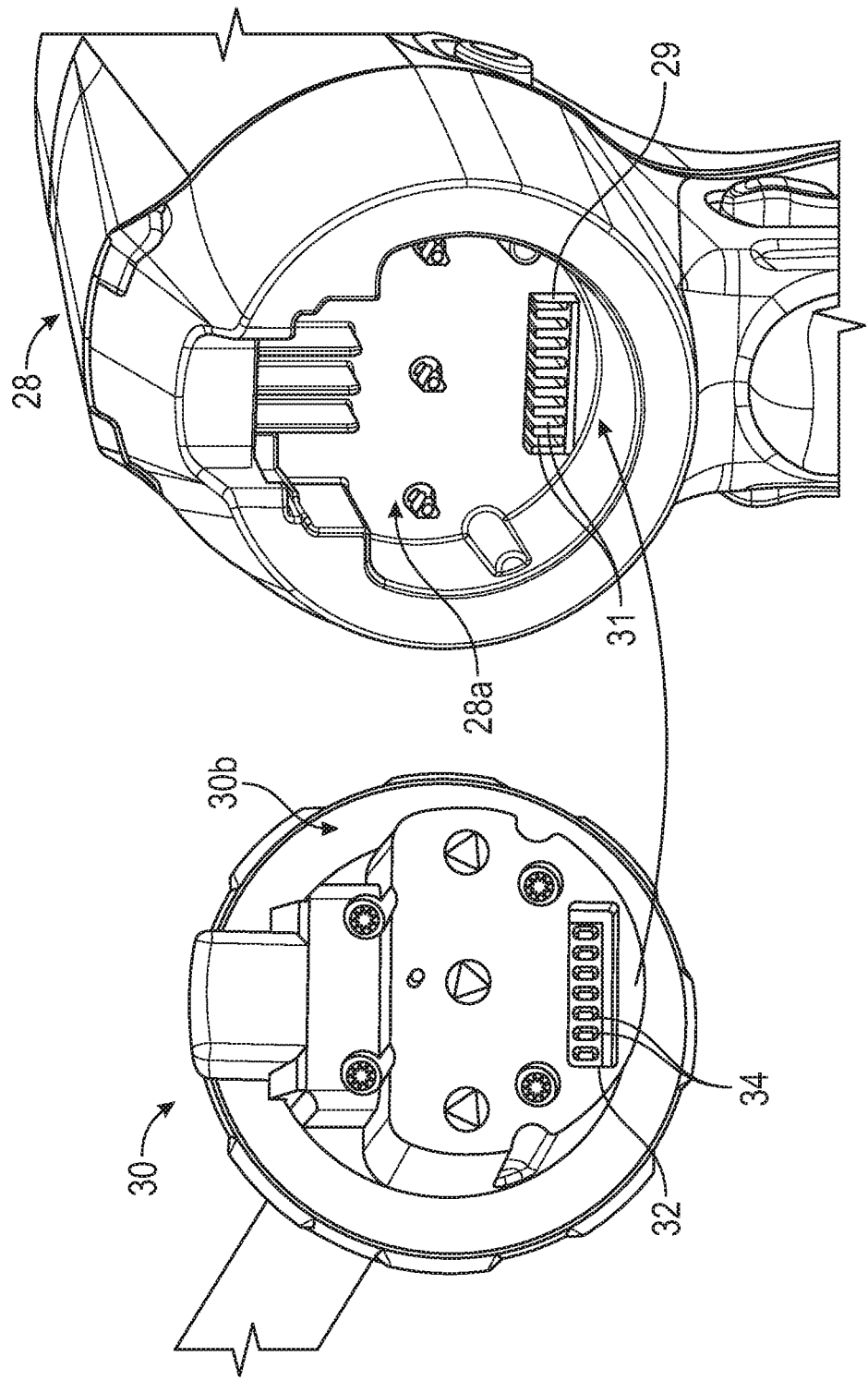
FIG. 2 is a perspective view illustrating a connection of the adapter assembly and the handle assembly of FIG. 1 according to an embodiment of the present disclosure.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
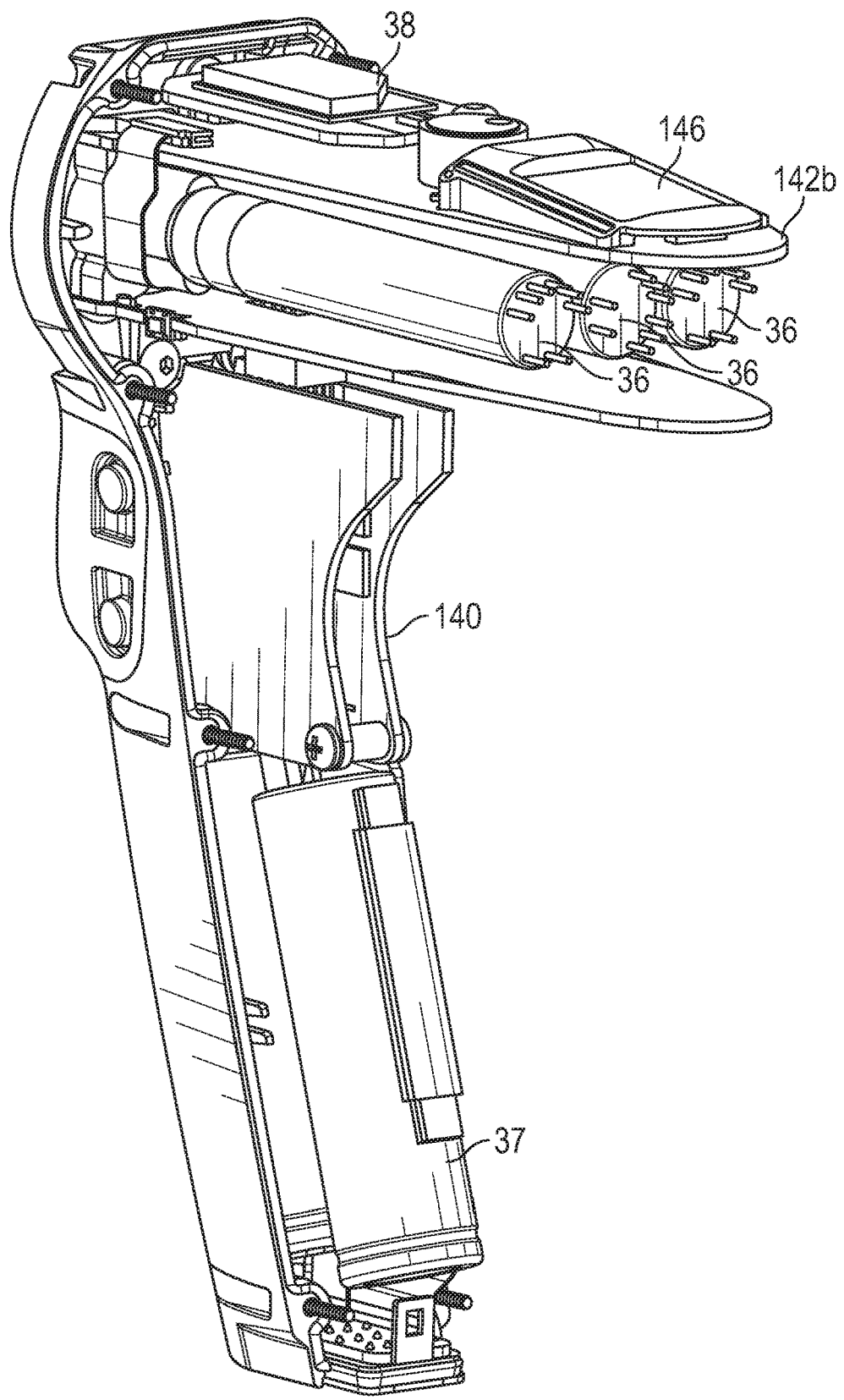
FIG. 3 is perspective view of internal components of the handle assembly according to an embodiment of the present disclosure.

With reference to FIG. 3, the handle assembly 20 includes one or more motors 36 which are coupled to a battery 37.

The handle assembly 20 also includes a main controller 38 for operating the motors 36 and other electronic components of the handle assembly 20, the adapter assembly 30, and the reload 40. The motors 36 are coupled to corresponding drive shafts 39 (FIG. 2), which are configured to engage sockets 33 on the proximal end portion 30b, such that rotation of the drive shafts 39 is imparted on the sockets 33. The actuation assembly 52 (FIG. 6) is coupled to one of the sockets 33. The actuation assembly 52 is configured to transfer rotational motion of the sockets 33 into linear motion and to actuate the reload 40 along with the anvil assembly 58. There are three actuation assemblies in the adapter assembly 30. The first actuation assembly is configured to convert rotational motion provided by the handle assembly 20 into axial translation useful for advancing/retracting the trocar member 50 slidably disposed within the distal end portion 30c of the adapter assembly 30. The second actuation assembly is configured to convert rotational motion provided by the handle assembly 20 into axial translation useful for advancing/retracting the staple band slidably disposed within the distal end portion 30c of the adapter assembly 30. The third actuation assembly is configured to convert rotational motion provided by the handle assembly 20 into axial translation useful for advancing/retracting a knife slidably disposed within the distal end portion 30c of the adapter assembly 30. The handle assembly 20 further includes a display screen 146 supported on main controller circuit board 142b. Display screen 146 is visible through a clear or transparent window.

Figure 4:
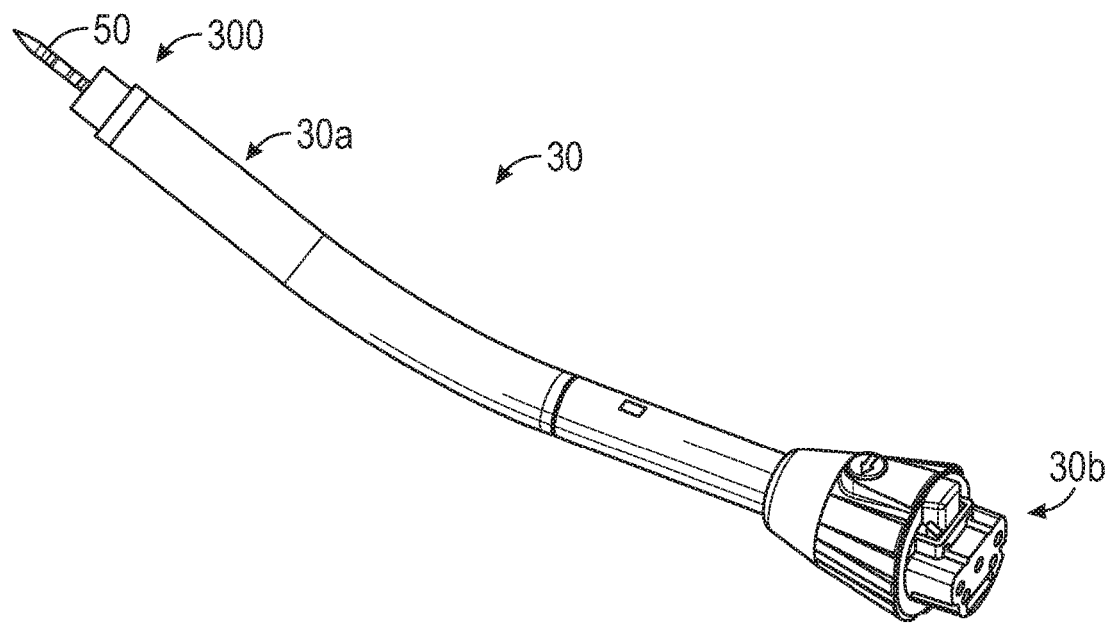
FIG. 4 is a perspective view of the adapter assembly of FIG. 1 without the reload according to an embodiment of the present disclosure.

With reference to FIG. 4, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the reload 40. In this manner, the adapter assembly 30 is configured to convert a rotational motion provided by the handle assembly 20 into axial translation useful for advancing/retracting a trocar member 50 slidably disposed within the distal end portion 30c of the adapter assembly 30 (FIG. 5) for firing staples of the reload 40.

With reference to FIG. 2, the connecting portion 28a includes an electrical receptacle 29 having a plurality of electrical contacts 31, which are in electrical communication with electronic (e.g., main controller 38) and electrical components (e.g., battery 37) of the handle assembly 20. The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 4, the trocar member 50 is slidably disposed within the tubular housing 30a of the adapter assembly 30 and extends past the distal end portion 30c thereof. In this manner, the trocar member 50 is configured for axial translation, which in turn, causes a corresponding axial translation of an anvil assembly 58 (FIG. 1) of the reload 40 to fire the staples (not shown) disposed therein. The trocar member 50 includes a proximal end which mates with the tubular housing 30a of the adapter assembly 30. A distal end portion of the trocar member 50 is configured to selectively engage the anvil assembly 58 of the reload 40 (FIG. 4). In this manner, when the anvil assembly 58 is connected to the trocar member 50, as will be described in detail hereinbelow, axial translation of the trocar member 50 in the first direction results in an opening of the reload 40, and axial translation of the trocar member 50 in a second, opposite direction, results in a closing of the reload 40.

Figure 5:
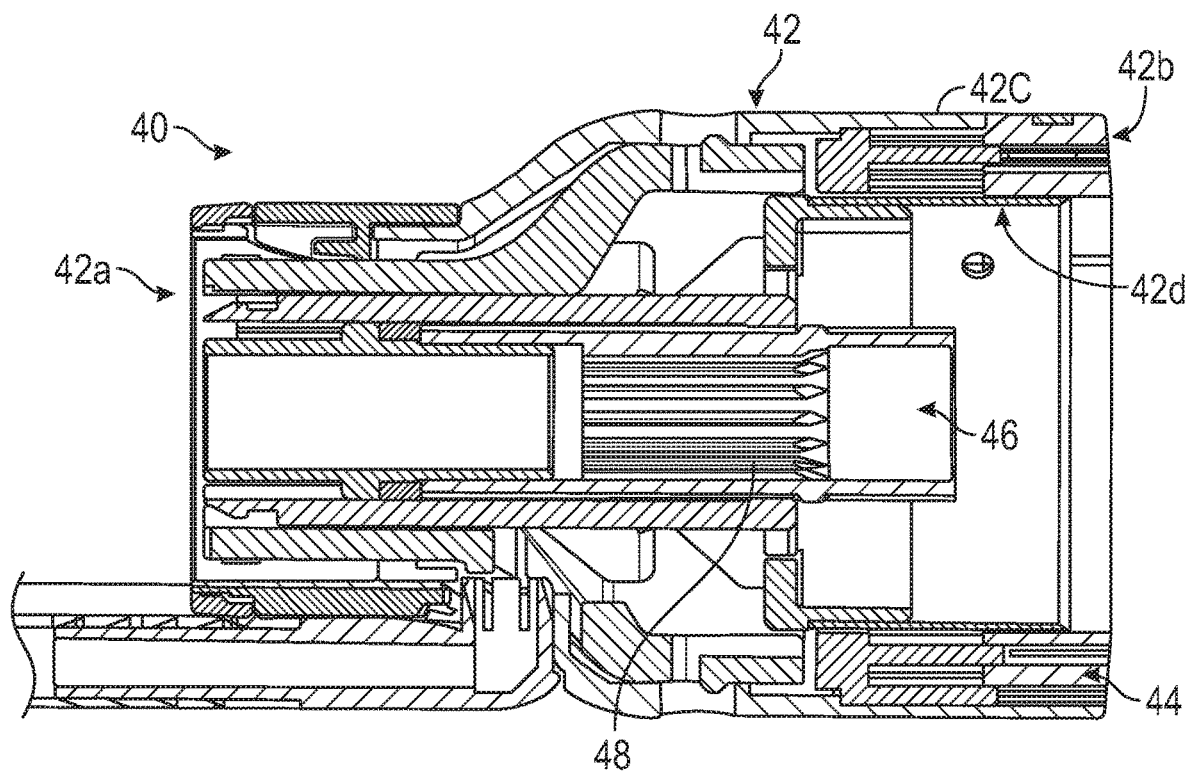
FIG. 5 is a side, cross-sectional view, of the reload of FIG. 1 according to an embodiment of the present disclosure.

As illustrated in FIGS. 1 and 5, the reload 40 is configured for operable connection to adapter assembly 30 and is configured to fire and form an annular array of surgical staples, and to sever a ring of tissue. The reload 40 includes a housing 42 having a proximal end portion 42a and a distal end portion 42b and a staple cartridge 44 fixedly secured to the distal end portion 42b of the housing 42. The proximal end portion 42a of the housing 42 is configured for selective connection to the distal end portion 30c of the adapter assembly 30 and includes a means for ensuring the reload 40 is radially aligned or clocked relative to the adapter assembly 30.

With reference to FIG. 5, the housing 42 of the reload 40 includes an outer cylindrical portion 42c and an inner cylindrical portion 42d. The outer cylindrical portion 42c and the inner cylindrical portion 42d of the reload 40 are coaxial and define a recess 46. The recess 46 of the reload 40 includes a plurality of longitudinally extending ridges or splines 48 projecting from an inner surface thereof which is configured to radially align the anvil assembly 58 relative to the reload 40 during a stapling procedure.

Figure 6:
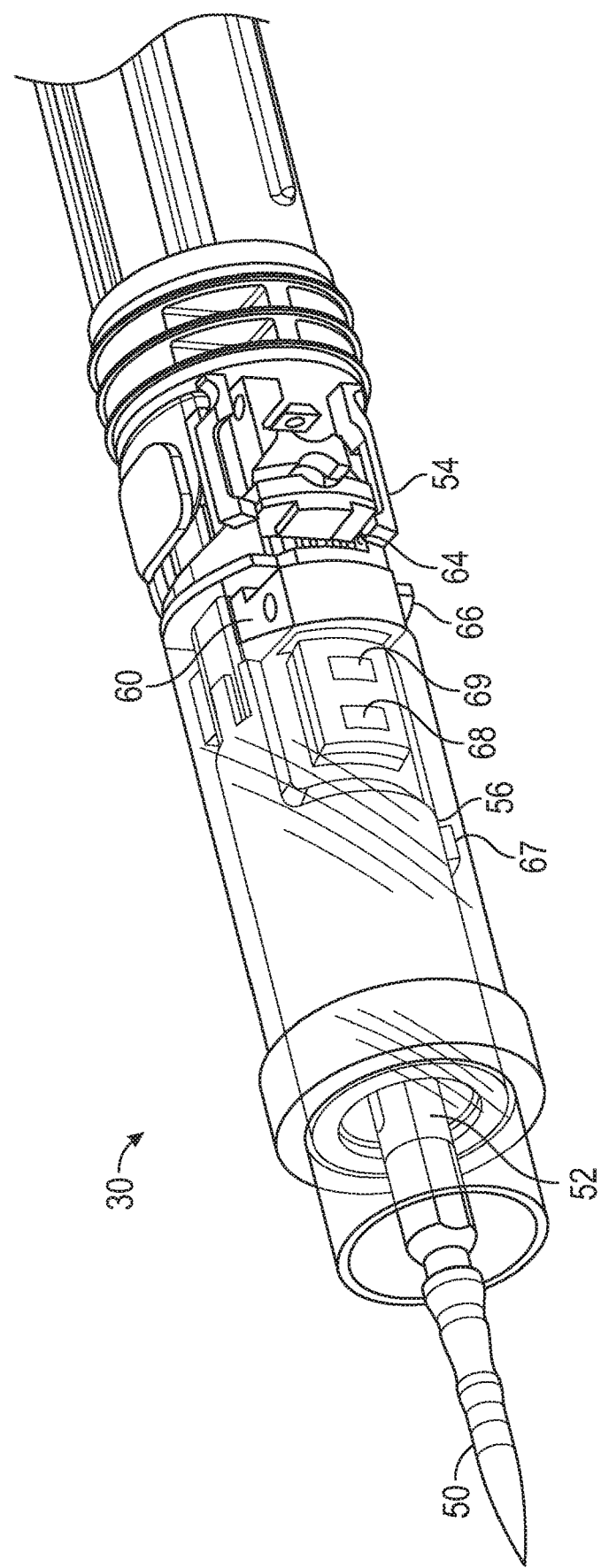
FIG. 6 is a perspective view of the distal end portion of the adapter assembly according to an embodiment of the present disclosure.

With reference now to FIG. 6, adapter assembly 30 includes an electrical assembly 60 disposed therewithin and configured for electrical connection with and between handle assembly 20 and reload 40. Electrical assembly 60 provides for communication (e.g., identifying data, life-cycle data, system data, load sense signals) with the main controller 38 of the handle assembly 20 through the electrical receptacle 29.

Electrical assembly 60 includes the electrical connector 32, a proximal harness assembly 62 having a ribbon cable, a distal harness assembly 64 having a ribbon cable, a load sensing assembly 66, and a distal electrical connector 67. The electrical assembly 60 also includes the distal electrical connector 67 which is configured to selectively mechanically and electrically connect to a chip assembly (not shown) of reload 40.

Electrical connector 32 of electrical assembly 60 is supported within the proximal end portion 30b of the adapter assembly 30. Electrical connector 32 includes the electrical contacts 34 which enable electrical connection to the handle assembly 20. Proximal harness assembly (not shown) is electrically connected to the electrical connector 32.

Load sensing assembly 66 is electrically connected to electrical connector 32 via proximal and distal harness assemblies (not shown). Shown in FIG. 6, the load sensing assembly 66 includes a sensor 68 and a memory 69. The sensor 68 is electrically connected to the memory 69. Load sensing assembly 66 is also electrically connected to distal harness assembly 64 via a sensor flex cable. As shown in FIG. 6, an actuation assembly 52, which is coupled to the trocar member 50, extends through the load sensing assembly 66. The load sensing assembly 66 provides strain measurements imparted on the adapter assembly 30 during movement of the trocar member 50, the anvil assembly 58, and other mechanical actuations, e.g., knife.

For a detailed description of an exemplary powered surgical stapler including an adapter assembly and a reload, reference may be made to commonly owned U.S. Patent Application Publication No. 2016/0310134 to Contini et al., titled "Handheld Electromechanical Surgical System," filed Apr. 12, 2016 incorporated by reference hereinabove.

Figure 7:
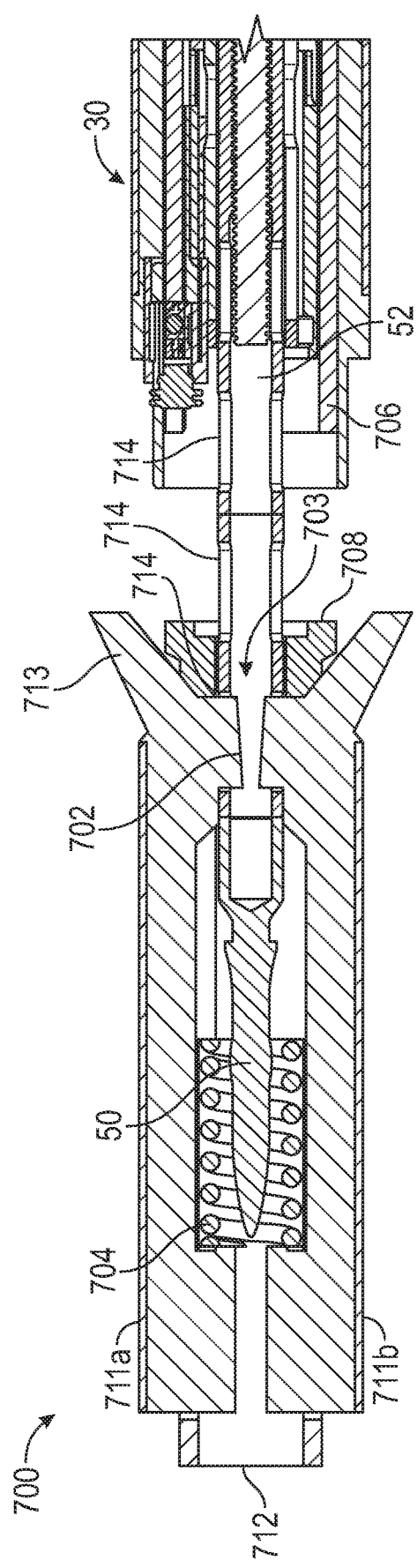
FIG. 7 is a side, cross-sectional view, of the distal end portion of the adapter assembly of FIG. 1 with a trocar member coupled to a calibration assembly according to an embodiment of the present disclosure.
Figure 8:
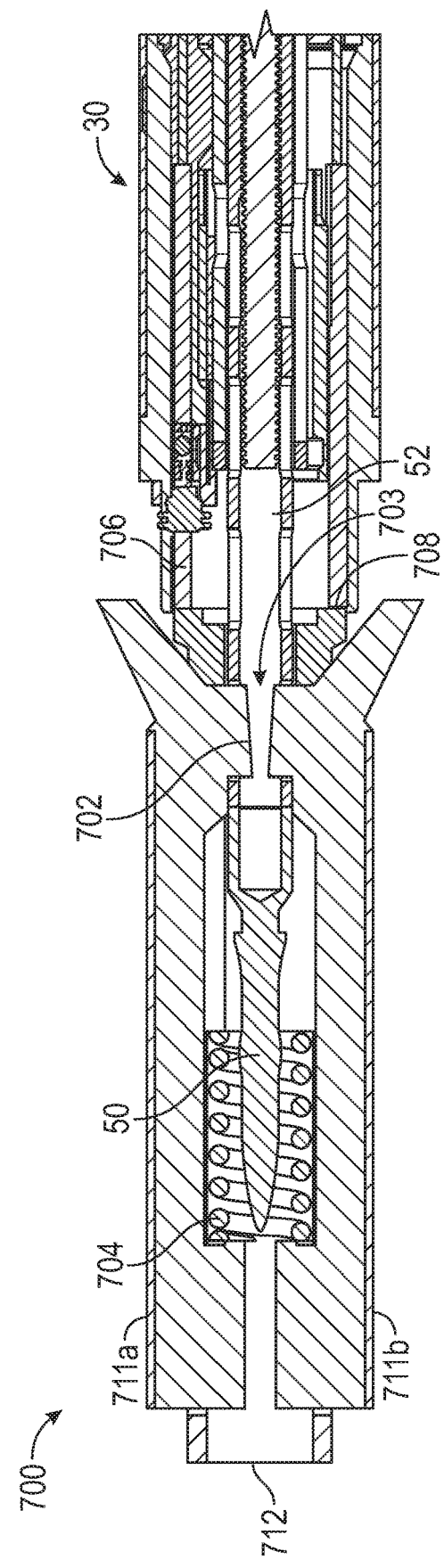
FIG. 8 is a side, cross-sectional view, of the distal end portion of the adapter assembly of FIG. 1 with the staple band making contact with the calibration assembly according to an embodiment of the present disclosure.
Figure 9:
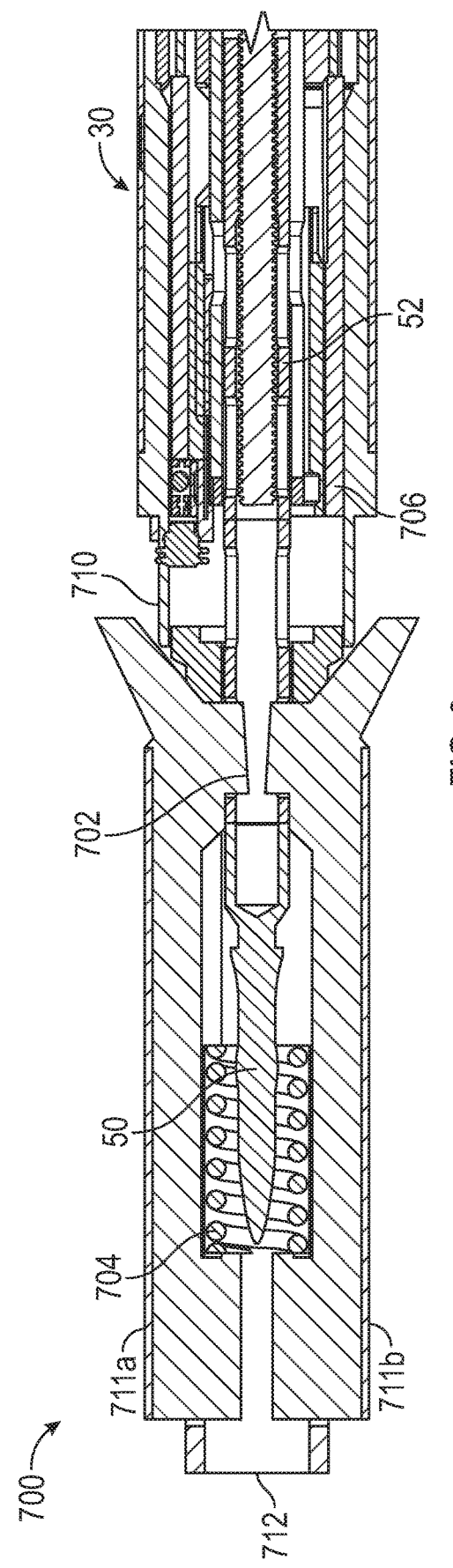
FIG. 9 is a side, cross-sectional view, of the distal end portion of the adapter assembly of FIG. 1 coupled to the calibration assembly, where the trocar member is retracted and the staple band is retracted according to an embodiment of the present disclosure.
Figure 10:
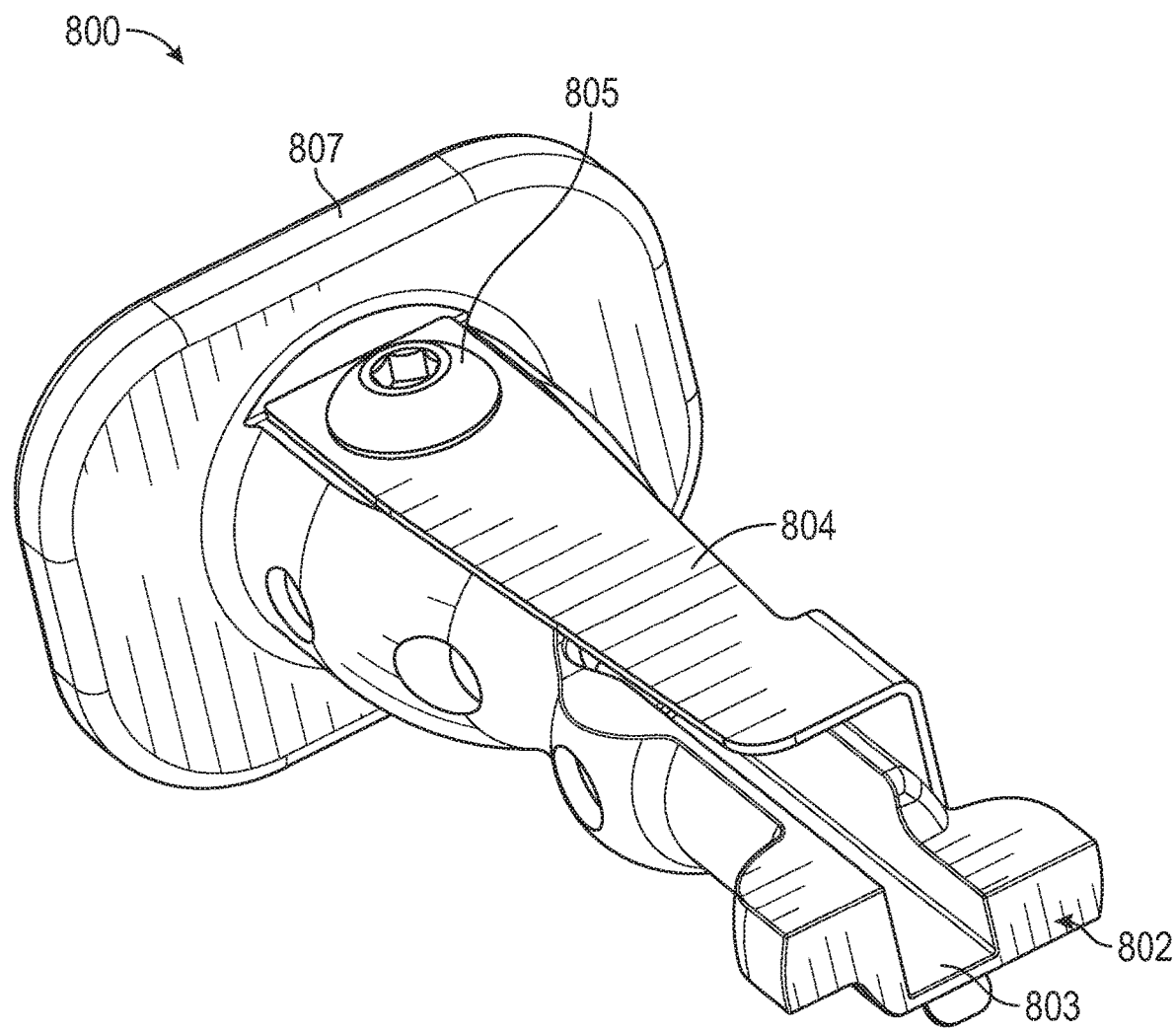
FIG. 10 is a perspective view of a distal portion of a calibration assembly according to another embodiment of the present disclosure.

FIGS. 7-9, depict an apparatus for ensuring strain gauge accuracy in accordance with the present disclosure. In one embodiment, the calibration assembly 700 includes a biasing member 704, having a predetermined spring load. The calibration assembly 700 includes a cylindrical housing 712, an opening 703 at a distal end, a loading area 708, and two opposing arms 711a, 711b. Located on the distal portion of each arm 711a, 711b is a catch 702 and an auto release latch 713 for moving the arms 711a and 711b apart. As the trocar member is extended through the opening 703 in the calibration assembly 700 as in FIG. 7, each of the catches 702 engages a corresponding opening 714 in the actuation assembly 52.

As shown in FIG. 8, when the trocar member 50 is retracted and the staple band 706 is extended, the calibration assembly 700 compresses the biasing member 704. The staple band 706 at this point is applying pressure to the loading area 708. The sensor 68 is calibrated by cycling power while the calibration assembly 700 is attached to the adapter assembly 30. The known spring load of the biasing member 704 and the sensing assembly 66 reading may be used to update the adapter assembly's memory 69 to apply the most recent conversion formula for the sensing assembly 66 electrical resistance to force correlation. This may be accomplished in several ways. In one embodiment, the known spring load of the biasing member 704 may be measured by the load sensing assembly 66 in the adapter assembly 30. The calibrated biasing member 704 deflects a certain known distance. The biasing member 704 signals a certain known force has been reached. In another embodiment, the known spring load may be stored in the memory 69 and used with the calculated distance the adapter assembly 30 has traveled, to calculate force. For example, multiple biasing members could be used with different spring loads, which bottom out at different differences, thus increasing the amount of data points that may be used for calibration.

A signal processing circuit is configured to calibrate the adapter assembly 30 with the calibration assembly 700 attached thereto by calculating a correction factor based on a comparison a force of the biasing member measured by the load sensing assembly 66 to the force value. The memory 69 of FIG. 6. stores the force measured by the load sensing assembly and the correction factor. The main controller 38 is configured to display the correction factor on the display screen 146 of FIG. 3. The main controller 38 uses the correction factor to adjust the measurements by the load sensing assembly 66 during use of the surgical instrument 10. As shown in FIG. 9, after calibration, when the staple band 706 is retracted, the trocar member 50 may be retracted, ejecting the calibration assembly 700 automatically, as the adapter assembly 30 cams off of the as the auto release latch 713.

FIGS. 10-13, depict an apparatus for ensuring strain gauge accuracy in accordance with the present disclosure. In an embodiment, the calibration assembly 800 of FIG. 10 has a hard stop, the loading surface 802, that the moving components of the adapter assembly 30 can apply pressure towards. The calibration assembly 800 flexes under load application, e.g., clamping, making the adapter assembly 30 itself act like a spring under load. The calibration assembly 800 includes an arm 804 having a latch 902, the arm is connected pivotally at a distal end portion of the calibration assembly 800 with a fastener 805. The calibration assembly 800 also includes an opening 803 at the proximal end for the trocar member 50 to be inserted and extended there through. The calibration assembly 800 has a tubular shape with a large flange 807 at the distal end for aiding a user during attachment of the calibration assembly 800 to the adapter assembly 30.

Figure 13:
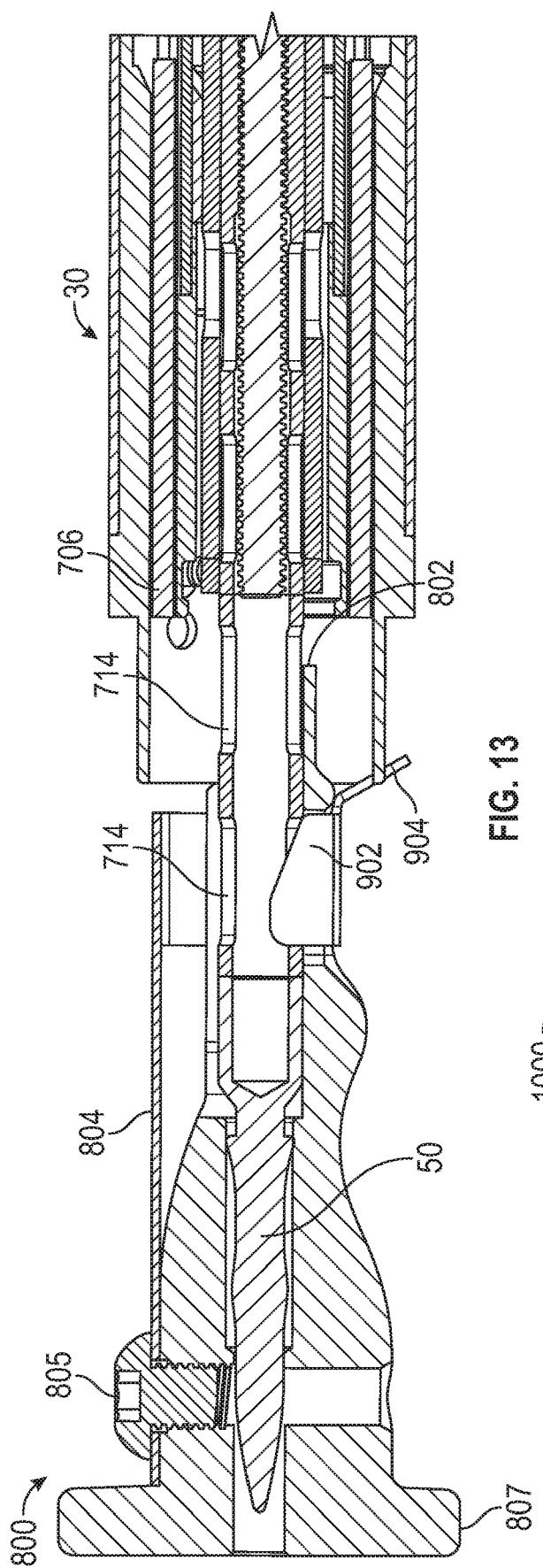
FIG. 13 is a side, cross-sectional view, of the distal end portion of the adapter assembly of FIG. 1 coupled with the calibration assembly of FIG. 10, where the trocar and the staple band are retracted, according to an embodiment the present disclosure.

Referring to FIGS. 11-13, a latch 902 engages the trocar member 30 as the trocar member is inserted into the calibration assembly 800. As shown in FIG. 11, the proximal end of the trocar member 50 is inserted into the opening 803 on the distal end of the calibration assembly 800. The latch 902 engages an opening 714 in the actuation assembly 52 as the trocar member 50 is extended. As shown in FIG. 12, the staple band 706 extends to contact the calibration assembly 800 before the trocar member 50 retracts fully. The loading surface 802 of the calibration assembly 800 makes contact with the staple band 706 starting the calibration load sequence. The load sensing assembly 66 measures a signal produced by flexing the adapter assembly 30 against the hard stop of the loading surface 802 of the calibration assembly 700, and stores this signal as a force value in the memory 69. The signal processing circuit is configured to determine if a relationship between the force value and the stored strain has changed. If a ratio between the force value and the stored strain changes, the signal processing circuit is configured to determine the deviation and store the deviation as a correction factor. The memory 69 stores the correction factor. The stored correction factor is then used to correct the stored strain.

The main controller 38 is configured to display the correction factor on the display screen 146 of FIG. 3. The main controller 38 uses the correction factor to adjust the measurements by the load sensing assembly 66 during use of the surgical instrument 10. As shown in FIG. 13 after load calibration, the staple band 706 is retracted and the trocar member 50 is continued to be pulled in. The calibration assembly 800 has a latch auto remove tab 904 that is used to cam the latch 902 off the trocar member 50.

While the adapter assembly 30 spring load may not be calibrated, recalling from memory 69 the previous loading measurements, the main controller 38 can check to see if signal from the load sensing assembly 66 and its relationship to the adapter assembly's 30 spring load has changed. If the ratio of strain gauge signal to the adapter assembly 30 spring load has degraded from its known ratio, the main controller 38 can recognize the deviation and either compensate, signal an error to the user, or decommission the adapter assembly 30. The known ratio may be calibrated in advance at manufacture. In order to compensate for the error, the main controller 38 utilizes the deviation to calculate a correction factor. This correction factor is stored in the memory 69 and may be used to correct for the deviation.

Figure 14:
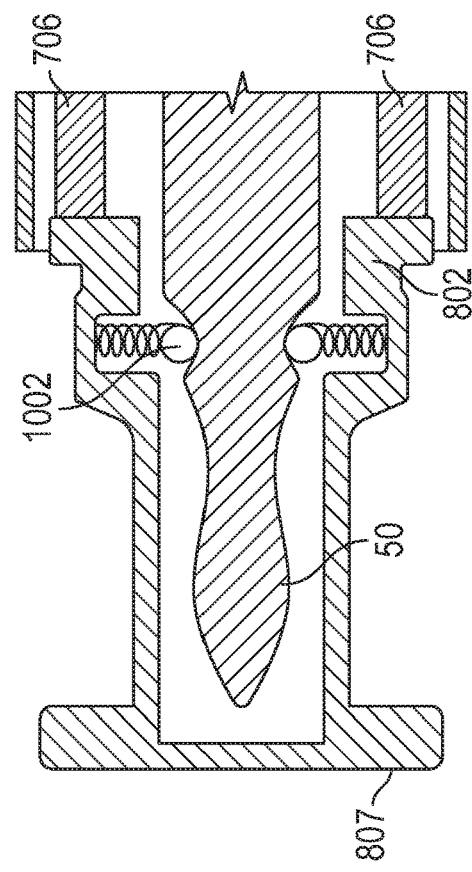
FIG. 14 is a side, cross-sectional view of the distal end portion of the adapter assembly of FIG. 1 coupled with a calibration assembly according to a further embodiment the present disclosure.

FIG. 14 depicts a side view of another embodiment of the distal end portion of the adapter assembly of FIG. 1 coupled to a calibration assembly 1000 according to an embodiment the present disclosure. A latching mechanism 1002, which Isa spring loaded mechanism, latches onto a trocar member 50, by inserting the trocar member 50 and having the staple band 706 contact the loading surface 802. The latching mechanism 1002 acts as a latch to hold the trocar member 50 in place. The calibration assembly 1000 may be pulled off of the trocar member 50 at a predetermined load, which indicates a force for load sensing assembly 66 calibration. This force may be measured by the load sensing assembly 66. This measured force may be stored in the memory 69 and the main controller 38 can compare this value to a stored value. Based on the difference between the stored value and the measured force, a correction factor may be calculated by the main controller 38. This correction factor is then stored in the memory 69, where it is used by the main controller 38 to compensate for the deviation in force. In an embodiment, a user could be notified of the error on the display screen 146 of FIG. 3, and/or the adapter assembly 30 could be decommissioned.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An apparatus for ensuring strain gauge accuracy comprising:
    a handle assembly including a controller;
    an adapter assembly including:
        a tubular housing having a proximal end portion configured to couple to the handle assembly and a distal end portion;
        a load sensing assembly configured to measure a load exerted on the tubular housing; and
        a signal processing circuit electrically coupled to the load sensing assembly;
    a memory coupled to the signal processing circuit; and
    a calibration assembly including a biasing member having a known spring rate stored as a force value in the memory, the calibration assembly configured to couple to the distal end portion of the adapter assembly;
    wherein the signal processing circuit is configured to calibrate the adapter assembly with the calibration assembly attached thereto by calculating a correction factor based on a comparison a force of the biasing member measured by the load sensing assembly to the force value.

2. The apparatus of claim 1, wherein the memory stores the force measured by the load sensing assembly and the correction factor.

3. The apparatus of claim 2, wherein the handle assembly includes a display and the signal processing circuit is configured to display the correction factor on the display.

4. The apparatus of claim 1, wherein the biasing member is selectable from a plurality of biasing members and is selectively couplable to the calibration assembly.

5. The apparatus of claim 1, wherein the correction factor is used to adjust a measurement by the load sensing assembly during use of the apparatus.

6. An apparatus for ensuring strain gauge accuracy comprising:
    a handle assembly including a controller;
    an adapter assembly including:
        a tubular housing having a proximal end portion configured to couple to the handle assembly and a distal end portion;
        a load sensing assembly configured to measure a load exerted on the tubular housing; and
        a signal processing circuit electrically coupled to the load sensing assembly;
    a memory coupled to the signal processing circuit, the memory storing at least one strain value; and
    a calibration assembly including a hard stop that the adapter assembly, the calibration assembly configured to couple to the distal end portion of the adapter assembly, such that the adapter assembly flexes under load while applying pressure on the hard stop;
    wherein the signal processing circuit is configured to calibrate the adapter assembly with the calibration assembly attached thereto by calculating a correction factor based on a deviation between the at least one strain value and a force value measured by the load sensing assembly during flexing of the adapter assembly under load while applying pressure on the hard stop.

7. The apparatus of claim 6, wherein the memory stores the correction factor.

8. The apparatus of claim 7, wherein the correction factor is used to correct the at least one strain value.

9. The apparatus of claim 8, wherein the handle assembly includes a display and the signal processing circuit is configured to display the correction factor on the display.

10. The apparatus of claim 8, wherein the correction factor is used to adjust a measurement by the load sensing assembly during use of the apparatus.

* * * * *